United States Patent [19]

Eyley et al.

[11] Patent Number: 4,618,715
[45] Date of Patent: Oct. 21, 1986

[54] PRODUCTION OF OXYGEN AND NITROGEN SUBSTITUTED BENZENES

[75] Inventors: Stephen C. Eyley; Stephen C. W. Coltman, both of Loughborough, England

[73] Assignee: Fisons Limited, Ipswich, England

[21] Appl. No.: 317,138

[22] Filed: Nov. 2, 1981

[30] Foreign Application Priority Data

Nov. 15, 1980 [GB] United Kingdom ............... 8036737

[51] Int. Cl.$^4$ .................... C07C 85/20; C07C 85/153
[52] U.S. Cl. .................................. 564/414; 564/223; 564/305; 564/443
[58] Field of Search ................ 564/305, 443, 223, 414

[56] References Cited

PUBLICATIONS

Feldman et al. (I), "Zhur. Obsch. Khim", vol. 23, pp. 2043-2046 (1953), translation supplied by applicants.
Olah et al., "Friedel-Crafts and Related Reactions", vol. III, Part I, pp. 1-11 and 56-59 (1964).
Feldman et al., "Chemical Abstracts", vol. 49, pp. 3063-3064 (1955).

Primary Examiner—Robert V. Hines
Attorney, Agent, or Firm—Marshall, O'Toole, Gerstein, Murray & Bicknell

[57] ABSTRACT

There is disclosed a process for the production of 3-amino-4,6-diacetyl phenol, or a derivative thereof, which comprises reacting a compound of formula III,

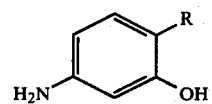

or a protected derivative thereof, in which R is acetyl or hydrogen, with an excess of acetyl chloride or acetyl bromide and aluminium chloride or aluminium bromide at a temperature of from 30° to 50° C. in an halogenated hydrocarbon solvent.

10 Claims, No Drawings

PRODUCTION OF OXYGEN AND NITROGEN SUBSTITUTED BENZENES

This invention relates to a novel process. Acetylation of already substituted benzene rings is a well known procedure, and is conventionally carried out by reaction of acetic acid, acetic anhydride or an acetyl halide with the appropriate substrate. It is also known that certain substituents deactivate the ring and thus make acetylation more difficult. Amongst these deactivating substituents is the acetyl group, and thus the production of di-acetyl compounds from an appropriate substrate carrying no, or one, acetyl substituent, would be expected to be a difficult reaction. Now with difficult reactions it is conventional to use higher reaction temperatures in order to 'force' the reaction to go. In the acetylation reactions mentioned above it has been conventional to use a Lewis acid catalyst, e.g. $ZnCl_2$, $FeCl_3$, $AlCl_3$, $TiCl_4$ etc. The reaction is normally carried out in a suitable solvent; one of the most common being carbon bisulphide. It has also been conventional to use an excess of the Lewis acid and of the acetylating agent, but clearly for reasons of economy the excess has normally not been more than a 1 or 2 fold excess.

In the production of an unsymmetrical di-acetyl compound from a corresponding mono-acetyl substrate, e.g. in the production of 3-amino-4,6-diacetyl phenol from a mono acetyl amino phenol there are clearly two possible starting materials, i.e. of formulae I and II,

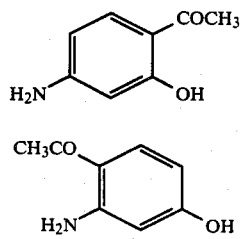

We have now surprisingly found that compounds of formula II cannot be acetylated to produce 3-amino-4,6-diacetyl phenol in any reasonable yield, and that compounds of formula I can only be acetylated to produce 3-amino-4,6-diacetyl phenol under very specific reaction conditions, i.e. using a particular acetylating agent, a narrow range of low temperatures, a particular solvent and a particular catalyst.

According to the invention we provide a process for the production of 3-amino-4,6-diacetyl phenol, or a derivative thereof, which comprises reacting a compound of formula III,

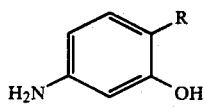

or a protected derivative thereof,
in which R is acetyl or hydrogen, with an excess of acetyl chloride or acetyl bromide and aluminium chloride or aluminium bromide at a temperature of from 30° to 50° C. in an halogenated hydrocarbon solvent. We prefer the reaction to be carried out at a temperature of from 40° to 45° C. At temperatures below about 30° C. the reaction proceeds too slowly for economic operation and at temperatures above about 50° C. the proportion of unwanted biproducts tends to increase.

We prefer to use a large excess of aluminium halide and acetyl halide. Thus we prefer to use from 5 to 20 equivalents, and more preferably about 10 equivalents, of aluminium halide (and also preferably of acetyl halide) with respect to the compound of formula III.

We prefer to use an initial concentration of above 0.05, and preferably from 0.2 to 0.3, moles per liter of the compound of formula III in the reaction mixture.

We prefer the halogenated hydrocarbon solvent to be 1,2-dichloroethane or more preferably dichloromethane. Dichloromethane is particularly preferred as its use makes temperature control of the reaction more simple.

When acetyl bromide is used we prefer also to use aluminium bromide as catalyst to avoid exchange reactions between acetyl bromide and aluminium chloride. However we prefer to use acetyl chloride and aluminium chloride. We also prefer to use equimolar proportions of the acetylating agent and the aluminium halide. However a 2 to 3 times molar excess of the acetylating agent with respect to the aluminium halide may be used if desired.

The reaction is preferably carried out under substantially anhydrous conditions, but small quantities of water will be absorbed by the excess acetyl halide.

When a derivative of the compound of formula III is used it may be a derivative of the —OH group, for example an ester or an ether, and preferably a C 1 to 6 alkyl ether, e.g. a methyl or butyl ether. A derivative of the —NH₂ group may also be used, e.g. an acyl derivative such as a C 1 to 6 alkanoyl (acetyl) derivative thereof. If desired both the —OH and —NH₂ groups may be in the form of a derivative. When a free —NH₂ group is used this group will be acetylated under the reaction conditions. We thus prefer to use 4-acetamido-2-hydroxyacetophenone as the starting material.

The reaction, when operated on a batch basis, is preferably allowed to continue for a period of from 20 to 50, e.g. about 40, hours, before the reaction product is isolated, e.g. by addition to water. The product may be isolated from the reaction mixture as a derivative of the —NH₂ or —OH group, e.g. as the —NH acetyl derivative. However the crude derivative of the —NH₂ group is preferably hydrolysed in situ to the free amino compound, e.g. by reaction with hydrochloric acid in an alcoholic solvent, e.g. ethanol, at an elevated temperature, e.g. of from about 80° to 110° C.

The 3-amino-4,6-diacetyl phenol, or the derivative thereof, may be isolated from the reaction mixture using conventional techniques known per se, e.g. by crystalisation, washing, drying etc.

Compounds of formula III are either known or may be made from known compounds using conventional techniques known per se.

3-Amino-4,6-diacetyl phenol is useful as an intermediate in the production of pharmaceuticals, e.g. 4,6-dioxo-4H,6H-pyrano[3,2-g]quinoline-2,8-dicarboxylic acids, which are of known utility as inter alia anti-allergic compounds. 3-Amino-4,6-diacetyl phenol is also useful as an intermediate in the production of other fine chemicals.

A further surprising feature of our invention is that no 3-amino-2,6-diacetyl phenol is found in the reaction product.

The invention is illustrated but in no way limited by the following Examples.

EXAMPLE 1

To a preformed acylating mixture comprising equimolar aluminium chloride and acetyl chloride in dichloromethane (270 ml/mole of AlCl₃) at 10°–15° C. was added 4-acetamido-2-hydroxyacetophenone (0.1 mole/mole of AlCl₃) over 15 minutes. The temperature was kept at less than 25° C.

The mixture was heated under reflux and the reaction monitored regularly by gas liquid chromatography. After 40 hours the mixture was allowed to cool to ambient temperature and was added to water (1 L/mole of AlCl₃) at a rate such that the temperature was maintained at 30°–35° C. The resulting slurry was stirred for 1 hour at 30° C. and the solid removed by filtration. This residue was washed with water, sucked dry and recrystallised from ethanol to afford, after drying in vacuo at 50° C., pure 3-acetamido-4,6-diacetylphenol as confirmed by gas liquid chromatography and proton nmr. Yield, 56%.

As an alternative the crude, damp product obtained by filtration of the slurry was dissolved in ethanol (ca13 liters per kg starting acetamide) at reflux and concentrated hydrochloric acid (0.7 liters/kg starting acetamide) was added. The reaction mixture was heated at reflux for 3½ hours. The mixture was cooled to room temperature and the crystalline product isolated, washed with ethanol, and dried. The product identity (as 3-amino-4,6-diacetylphenol) was confirmed by gas liquid chromatography, and by infra-red and proton nmr. Yield 60% based on starting 4-acetamido-2-hydroxyacetophenone.

EXAMPLE 2

Acetylation of 3-aminophenol

Finely pulverised 3-aminophenol was added over a few minutes to a solution of aluminium chloride and acetyl chloride (equimolar proportions of each, 10 equivalents per equivalent of 3-aminophenol) in dichloromethane (dried over CaCl₂, 1.5 liter per kg AlCl₃), at room temperature. The reaction mixture was heated to reflux point for 3 days. The reaction mixture was then cooled to room temperature and poured into water (2 liters per liter of reaction mixture) and extracted with dichloromethane.

The 3-acetamido-4,6-diacetyl phenol product was isolated from the organic phase by extraction with aqueous potassium carbonate and characterised by its glc properties and NMR spectrum.

EXAMPLE 3

Diacetylation of 3-acetamidoanisole

To a preformed acylating mixture comprising equimolar aluminium chloride and acetyl chloride in dichloromethane (150 ml/mole AlCl₃) was added a solution of 3-acetamidoanisole (0.1 mole mole AlCl₃) in dichloromethane (125 ml/mole AlCl₃) over 40 minutes, maintaining the temperature of the reaction mixture at 0°–5° C.

The mixture was heated under reflux and the reaction monitored by glc. After 70 hrs the mixture was allowed to cool and added to ice-water. 4-Acetamido-2-hydroxyacetophenone was removed by filtration. The aqueous layer was extracted with methylene chloride, the organic phase washed with water, dried and concentrated. Recrystallisation from ethanol afforded, after drying, pure 3-acetamido-4,6-diacetylphenol, confirmed by glc and NMR.

Representative yields

4-Acetamido-2-hydroxyacetophenone: 38%
1 3-Acetamido-4,6-diacetylphenol: 34%

The 4-acetamido-2-hydroxyacetophenone can, if desired, be recycled or further acetylated to produce the desired product.

The 3-acetamido-4,6-diacetylphenol may be converted to 3-amino-4,6-diacetylphenol using conventional techniques known per se, e.g. as in Example 1.

We claim:

1. A process for the production of 3-amino-4,6-diacetyl phenol, or a derivative thereof, which comprises reacting a compound of formula III,

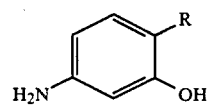

or a protected derivative thereof, in which R is acetyl or hydrogen, with an excess of acetyl chloride or acetyl bromide and aluminium chloride or aluminium bromide at a temperature of from 30° to 50° C. in an halogenated hydrocarbon solvent.

2. A process according to claim 1, wherein acetyl chloride and aluminium chloride are used.

3. A process according to claim 2, wherein the solvent is methylene chloride.

4. A process according to claim 3, wherein there is used from 5 to 20 equivalents of aluminium chloride and acetyl chloride with respect to the compound of formula III.

5. A process according to claim 1, wherein an initial concentration of from 0.2 to 0.3 moles per liters of the compound of formula III is used.

6. A process according to claim 1, wherein the compound of formula III is used in the form of an acyl derivative of the —NH₂ group.

7. A process according to claim 6, wherein the compound of formula III is 4-acetamido-2-hydroxyacetophenone.

8. A process according to claim 1, wherein the reaction is carried out at a temperature of from 40° to 45° C.

9. A process according to claim 1, wherein the reaction product is hydrolysed to free 3-amino-4,6-diacetyl phenol.

10. A process for the production of 3-amino-4,6-diacetyl phenol, or a derivative thereof, which comprises reacting a compound of formula III,

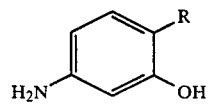

or a protected derivative thereof,
in which R is acetyl or hydrogen, with at least five equivalents of acetyl chloride or acetyl bromide and with at least five equivalents or aluminium chloride or aluminium bromide at a temperature of from 30° to 50° C. in an halogenated hydrocarbon solvent.

* * * * *